United States Patent [19]

Hoffmann et al.

[11] 4,164,575
[45] Aug. 14, 1979

[54] COMBATING PESTS WITH O-ALKYL-O-TRIFLUOROMETHYLSUL-PHINYLPHENYL-THIONO(THIOL)-PHOSPHORIC ACID ESTERS

[75] Inventors: Hellmut Hoffmann, Wuppertal; Erich Klauke, Odenthal; Ingeborg Hammann, Cologne; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 883,001

[22] Filed: Mar. 3, 1978

[30] Foreign Application Priority Data

Mar. 8, 1977 [DE] Fed. Rep. of Germany ....... 2709932

[51] Int. Cl.² ............................ A01N 9/36; C07F 9/17
[52] U.S. Cl. .................................... 424/216; 260/949
[58] Field of Search ......................... 260/949; 424/216

[56] References Cited

U.S. PATENT DOCUMENTS 4,067,972  1/1978  Oswald et al. ........................ 424/216

FOREIGN PATENT DOCUMENTS 7301018  7/1973  Netherlands ............................. 424/216

Primary Examiner—Anton H. Sutto
Attorney, Agent, or Firm—Sprung, Felfe, Horn, Lynch & Kramer

[57] ABSTRACT

O-Alkyl-O-trifluoromethylsulphinylphenyl-thiono (thiol)-phosphoric acid esters of the formula

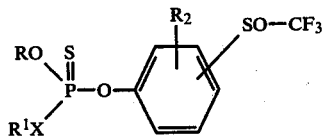

wherein
R and R¹ each independently is alkyl,
R² is hydrogen, halogen or alkyl, and
X is oxygen or sulphur, which possess arthropodicidal and nematicidal properties.

10 Claims, No Drawings

COMBATING PESTS WITH O-ALKYL-O-TRIFLUOROMETHYLSULPHINYL-PHENYL-THIONO(THIOL)-PHOSPHORIC ACID ESTERS

The present invention relates to and has for its objects the provision of particular new O-alkyl-O-trifluoromethylsulphinylphenyl-thiono (thiol)-phosphoric acid esters which possess arthropodicidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is already known that certain trifluoromethylthio- and alkylthio-phenyl(thiono)-phosphoric(phosphonic) acid esters, for example O-ethyl-O-(2-methyl-4-trifluoromethylthiophenyl)-thionoethanephosphonic acid ester, O,O-dimethyl-O-(3-methyl-4-methylthio-phenyl)-thiono- and O,O-diethyl-O-(4-trifluoro-methylthiophenyl)-phosphoric acid ester, possess insecticidal and acaricidal properties (see German Auslegeschriften (German Published Specifications) Nos. 1,153,747 and 1,116,656).

The present invention now provides, as new compounds, the trifluoromethylsulphinylphenylthiono(thiol)-phosphoric acid esters of the general formula

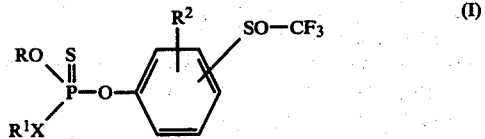

in which

R and R$^1$, which may be identical or different, each represent alkyl,

R$^2$ represents hydrogen, halogen or alkyl and

X represents oxygen or sulphur.

Preferably, R represents straight-chain or branched alkyl with 1 to 6 (especially 1 to 3) carbon atoms, R$^1$ represents straight-chain or branched alkyl with 1 to 6 (especially 1 to 4) carbon atoms and R$^2$ represents hydrogen, chlorine or methyl.

Surprisingly, the trifluoromethylsulphinylphenylthiono-(thiol)-phosphoric acid esters according to the invention exhibit a better insecticidal, acaricidal and nematicidal action than the trifluoromethylthio- and alkylthiophenyl-(thiono)-phosphoric(phosphonic) acid esters of analogous structure, and of the same type of action, which were previously known from the literature. The compounds according to the present invention thus represent a genuine enrichment of the art.

The invention also provides a process for the preparation of a trifluoromethylsulphinylphenylthiono(thiol)-phosphoric acid ester of the formula (I) in which a thiono(thiol)-phosphoric acid ester halide of the general formula

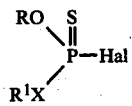

in which

R, R$^1$ and X have the above-mentioned meanings and

Hal represents, preferably chlorine, is reacted, if appropriate in the presence of a solvent or diluent, with a trifluoromethylsulphinylphenol of the general formula

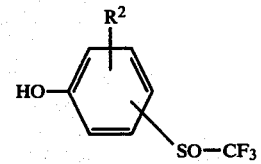

in which

R$^2$ has the above-mentioned meaning, the latter being employed in the form of an alkali metal salt, alkaline earth metal salt or ammonium salt or as such in the presence of an acid acceptor.

If, for example, O-ethyl-S-sec.-butyl-thionothiolphosphoric acid diester chloride and 2-methyl-4-trifluoromethylsulphinyl-phenol are used as starting materials, the course of the reaction can be represented by the following equation:

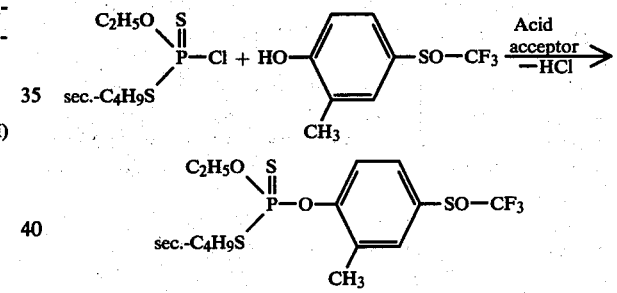

The thiono(thiol)-phosphoric acid ester halides (II) to be used as starting materials are known and can be prepared in accordance with known processes. The following may be mentioned as individual examples thereof: O,O-dimethyl-, O,O-diethyl-, O,O-di-n-propyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O-methyl-O-tert.-butyl-, O-ethyl-O-n-propyl-, O-ethyl-O-isopropyl-, O-ethyl-O-n-butyl-, O-ethyl-O-sec.-butyl-, O-ethyl-O-iso-butyl-, O-n-propyl-O-butyl- and O-iso-propyl-O-butyl-thionophosphoric acid diester chloride, and O,S-dimethyl-, O,S-diethyl-, O,S-di-n-propyl-, O,S-di-iso-propyl-, O-ethyl-S-n-propyl-, O-ethyl-S-isopropyl-, O-ethyl-S-n-butyl-, O-ethyl-S-sec.-butyl-, O-n-propyl-S-ethyl-, O-n-propyl-S-iso-propyl-, O-methyl-S-n-propyl- and O-methyl-S-ethyl-thionothiolphosphoric acid diester chlorides.

The trifluoromethylsulphinylphenols (III) to be used as starting materials are also known and can be prepared in accordance with processes known from the literature. The following may be mentioned as individual examples thereof: 4-trifluoromethylsulphinyl-phenol, 3-methyl-4-trifluoromethylsulphinyl-phenol, 2-methyl-4-trifluoromethyl-sulphinyl-phenol, 2-chloro-4-trifluoromethylsulphinyl-phenol and 3-chloro-4-trifluoromethylsulphinyl-phenol.

The preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at from 0° to 100° C., preferably at from 15° to 60° C.

In general, the reaction is allowed to take place under normal pressure.

To carry out the process, the starting materials are in most cases employed in stoichiometric amounts. An excess of either reactant produces no significant advantages. In most cases, the reactants are brought together in one of the above-mentioned solvents and are stirred, in most cases at elevated temperature, for one or more hours to complete the reaction.

Thereafter the reaction mixture is poured into water and is extracted by shaking with an organic solvent, for example toluene. The organic phase is then worked up in the usual manner by washing, drying and distilling off the solvent.

The new compounds are obtained in the form of oils which, in a number of cases, cannot be distilled without decomposition, but are freed from the last volatile constituents by so-called "incipient distillation", that is to say by prolonged heating under reduced pressure to moderately elevated temperatures, and are purified in this manner. They are characterized by the refractive index.

As already mentioned, the compounds according to the present invention are distinguished by an excellent insecticidal, acaricidal and nematicidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example Oniscus asellus, Armadillidium vulgare and Porcellio scaber;

from the class of the Diplopoda, for example Blaniulus guttulatus;

from the class of the Chilopoda, for example Geophilus carpophagus and Scutigera spec.;

from the class of the Symphyla, for example Scutigerella immaculata;

from the order of the Thysanura, for example Lepisma saccharina;

from the order of the Collembola, for example Onychiurus armatus;

from the order of the Orthoptera, for example Blatta orientalis, Periplaneta americana, Leucophaea maderae, Blattella germanica, Acheta domesticus, Gryllotalpa spp., Locusta migratoria migratorioides, Melanoplus differentialis and Schistocerca gregaria;

from the order of the Dermaptera, for example Forficula auricularia;

from the order of the Isoptera, for example Reticulitermes spp.;

from the order of the Anoplura, for example Phylloxera vastatrix, Pemphigus spp., Pediculus humanus corporis, Haematopinus spp. and Linognathus spp.;

from the order of the Mallophaga, for example Trichodectes spp. and Damalinea spp.;

from the order of the Thysanoptera, for example Hercinothrips femoralis and Thrips tabaci;

from the order of the Heteroptera, for example Eurygaster spp., Dysdercus intermedius, Piesma quadrata, Cimex lectularius, Rhodnius prolixus and Triatoma spp.;

from the order of the Homoptera, for example Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp.;

from the order of the Lepidoptera, for example Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima and Tortrix viridana;

from the order of the Coleoptera, for example Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psyll-

*oides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

When used against nematodes, the preparations are generally applied to an area of agriculture in amounts of 1 to 100 kg of active compound per hectare, and are then incorporated into the soil.

It will be realized, of course, that the concentration of the particular active compound utilized in admixture with the carrier vehicle will depend upon the intended application. Therefore, in special cases it is possible to go above or below the aforementioned concentration ranges.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or nematodes which comprises applying to the arthropods or nematodes, or to a habitat thereof, a compound of the present invention alone or in the form of a composition containing as active ingredient a compound of the present invention, in admixture with a diluent or carrier.

The present invention also provides a method of freeing or protecting domesticated animals from ectoparasitical insects or acarids which comprises applying to said animals a compound according to the present invention, in admixture with a diluent or carrier.

The preparation of the new compounds of the present invention is illustrated, without limitation, by the following example:

EXAMPLE 1

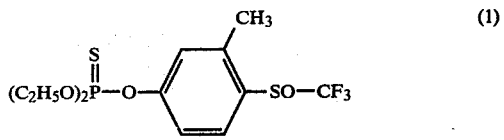
(1)

19 g (0.1 mol) of O,O-diethylthionophosphoric acid diester chloride were rapidly added dropwise to a slurry of 23 g (0.1 mol) of 3-methyl-4-trifluoromethyl-sulphinylphenol and 15 g of potassium carbonate in 150 ml of acetonitrile, in the course of which the temperature rose to 45° C. The reaction mixture was then stirred for a further 4 hours at room temperature, poured into water and taken up in toluene, and the phases were separated. The organic phase was dried over sodium sulphate, the toluene was stripped off in vacuo and the residue was subjected to incipient distillation. 33 g (88% of theory) of O,O-diethyl-O-(3-methyl-4-trifluoromethylsulphinyl-phenyl)-thionophosphoric acid ester having a refractive index $n_D^{29}$ of 1.5069 were thus obtained.

The following compounds of the formula

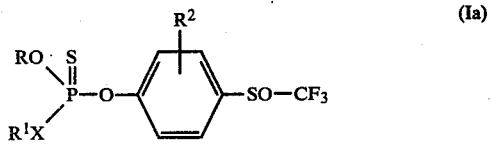
(Ia)

could be prepared analogously to Example 1:

TABLE 1

| Compound No. | R | $R^1$ | $R^2$ | X | Refractive index: | Yield (% of theory) |
|---|---|---|---|---|---|---|
| 2 | $C_2H_5$ | $C_2H_5$ | H | O | $n_D^{29}$:1.5015 | 86 |
| 3 | $C_2H_5$ | $n-C_3H_7$ | 3-$CH_3$ | S | $n_D^{29}$:1.5374 | 84 |
| 4 | $C_2H_5$ | $n-C_3H_7$ | H | S | $n_D^{29}$:1.5350 | 84 |
| 5 | $CH_3$ | $CH_3$ | H | O | $n_D^{31}$:1.5120 | 81 |
| 6 | $CH_3$ | $CH_3$ | 3-$CH_3$ | O | $n_D^{31}$:1.5193 | 83 |

O-n-Butyl-O-iso-propyl-O-(4-chloro-3-trifluoromethylsulphinyl-phenyl)-thionophosphoric acid ester can be similarly prepared.

The insecticidal, acaricidal and nematicidal activity of the compounds of this invention is illustrated by the following examples wherein the compounds according to the present invention are each identified by the number (given in brackets) from Example 1, hereinabove.

The known comparison compounds are identified as follows:

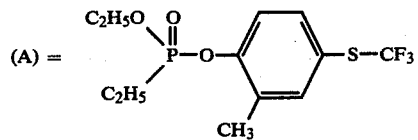

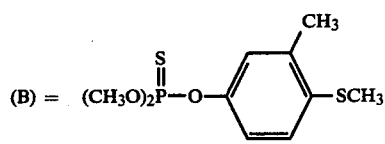

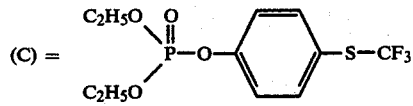

EXAMPLE 2

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (Brassica oleracea) which had been heavily infested with peach aphids (Myzus persicae) were sprayed with the preparation of the active compound until dripping wet.

After the specified periods of time, the degree of destruction was determined as a percentage: 100% meant that all of the aphids were killed whereas 0% meant that none of the aphids were killed.

The active compounds, the concentrations of the active compounds, the evaluation times and the results can be seen from the following table:

Table 2

| | Insects which damage plants (Myzus test) | |
|---|---|---|
| Active Compounds | Active compound concentration in % | Degree of destruction in % after 1 day |
| (A) | 0.1 | 100 |
| | 0.01 | 0 |
| (5) | 0.1 | 100 |
| | 0.01 | 100 |
| (6) | 0.1 | 100 |
| | 0.01 | 100 |
| (2) | 0.1 | 100 |
| | 0.01 | 98 |
| (1) | 0.1 | 100 |
| | 0.01 | 99 |
| (4) | 0.1 | 100 |
| | 0.01 | 98 |

Table 2-continued

| Active Compounds | Insects which damage plants (Myzus test) Active compound concentration in % | Degree of destruction in % after 1 day |
|---|---|---|
| (3) | 0.1 | 100 |
|  | 0.01 | 100 |

EXAMPLE 3

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 3

| Active compounds | (Mites which damage plants) Tetranychus test Active compound concentration in % | Degree of destruction in % after 2 days |
|---|---|---|
| (B) | 0.1 | 0 |
| (2) | 0.1 | 100 |
| (1) | 0.1 | 98 |
| (4) | 0.1 | 100 |
| (3) | 0.1 | 98 |

EXAMPLE 4

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The amount of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

The active compounds, the amounts used and the results can be seen from the table which follows:

Table 4

| Active compounds | (Soil insecticides) *Tenebrio molitor* larvae in the soil Degree of destruction in % at an active compound concentration of 5 ppm |
|---|---|
| (B) | 0 |
| (C) | 0 |
| (1) | 100 |
| (2) | 100 |
| (3) | 100 |
| (4) | 100 |

EXAMPLE 5

Test nematode: *Meloidogyne incognita* Solvent: 3 parts by weight of acetone Emulsifier: 1 part by weight of alkylarly polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

Table 5

| Active compounds | (Nematicides) *Meloidogyne incognita* Degree of destruction in % at an active compound concentration of 1.25 ppm |
|---|---|
| (B) | 0 |
| (1) | 100 |
| (2) | 100 |

EXAMPLE 6

Test with parasitic fly larvae
Emulsifier: 80 parts by weight of Cremophor El

To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction in % was determined. 100% meant that all of the larvae had been killed and 0% meant that none of the larvae had been killed.

The active compound, amounts used and results can be seen from the table which follows:

Table 6

Test with parasitic fly larvae

| Active compound | Active compound concentration in ppm | Destructive action in % |
|---|---|---|
| (5) | 100 | 100 |
|  | 30 | 100 |
|  | 10 | 100 |
|  | 3 | 100 |
|  | 1 | 100 |
|  | 0.3 | 100 |
|  | 0.1 | 100 |

It will be appreciated that the instant specification and examples are set forth by way of illustration and not limitation, and that various modifications and changes may be made without departing from the spirit and scope of the present invention.

What we claim is:

1. An O-alkyl-O-trifluoromethylsulphinylphenylthiono(thiol)-phosphoric acid ester of the formula

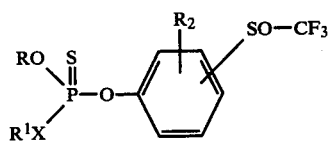

wherein
R and R¹ each independently is alkyl,
R² is hydrogen, halogen or alkyl, and
X is oxygen or sulphur.

2. A method of combating arthropods or nematodes which comprises applying to the arthropods or nematodes, or to a habitat thereof, an arthropodicially or nematicidally effective amount of an ester according to claim 1.

3. An ester according to claim 1,
wherein
R is alkyl with 1 to 6 carbon atoms,
R¹ is alkyl with 1 to 6 carbon atoms, and
R² is hydrogen, chlorine or methyl.

4. An ester according to claim 1 wherein such ester is O,O-diethyl-O-(3-methyl-4-trifluoromethylsulphinyl-phenyl)-thionophosphoric acid ester of the formula

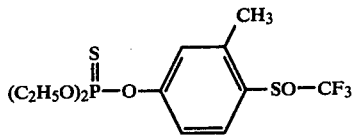

5. An ester according to claim 1 wherein such ester is O,O-diethyl-O-(4-trifluoromethylsulphinyl-phenyl)-thionophosphoric acid ester of the formula

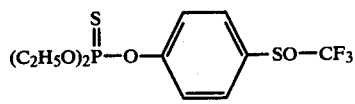

6. An ester according to claim 1 wherein such ester is O-ethyl-S-n-propyl-O-(4-trifluoromethylsulphinyl-phenyl)-thionothiolphosphoric acid ester of the formula

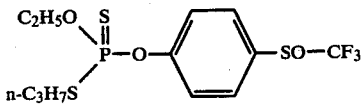

7. An ester according to claim 1 wherein such ester is O,O-dimethyl-O-(4-trifluoromethylsulphinyl-phenyl)-thionophosphoric acid ester of the formula

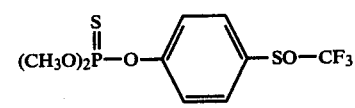

8. An ester according to claim 1 wherein such ester is O,O-dimethyl-O-(3-methyl-4-trifluoromethylsulphinyl-phenyl)-thionophosphoric acid ester of the formula

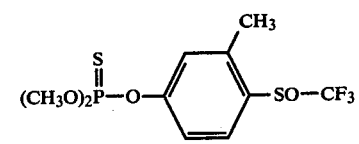

9. An arthropodicidal or nematicidal composition containing as active ingredient an arthropodicially or nematicidally effective amount of an ester according to claim 1 in admixture with a diluent.

10. The method according to claim 2 wherein to a domesticated animal to be freed or protected from ectoparasicital insects or acarids there is applied
O,O-diethyl-O-(3-methyl-4-trifluoromethylsulphinyl-phenyl)-thionophosphoric acid ester,
O,O-diethyl-O-(4-trifluoromethylsulphinyl-phenyl)-thionophosphoric acid ester,
O-ethyl-S-n-propyl-O-(4-trifluoromethylsulphinyl-phenyl)-thionothiolphosphoric acid ester,
O,O-dimethyl-O-(4-trifluoromethylsulphinyl-phenyl)-thionophosphoric acid ester, or
O,O-dimethyl-O-(3-methyl-4-trifluoromethylsulphinyl-phenyl)-thionophosphoric acid ester.

* * * * *